(12) United States Patent
Levin et al.

(10) Patent No.: US 7,981,684 B2
(45) Date of Patent: Jul. 19, 2011

(54) METHODS AND BIOMARKERS FOR DIAGNOSING AND MONITORING PSYCHOTIC DISORDERS

(75) Inventors: Yishai Levin, Cambridge (GB); Sabine Bahn, Cambridge (GB)

(73) Assignee: Psynova Neurotech Limited, Cambridge (GB)

( * ) Notice: Subject to any disclaimer, the term of this patent is extended or adjusted under 35 U.S.C. 154(b) by 0 days.

(21) Appl. No.: 12/523,842

(22) PCT Filed: Jan. 21, 2008

(86) PCT No.: PCT/GB2008/000199
§ 371 (c)(1),
(2), (4) Date: Jan. 12, 2010

(87) PCT Pub. No.: WO2008/090319
PCT Pub. Date: Jul. 31, 2008

(65) Prior Publication Data
US 2010/0129919 A1  May 27, 2010

(30) Foreign Application Priority Data

Jan. 22, 2007 (GB) .................................. 0701626.4

(51) Int. Cl.
*G01N 33/53* (2006.01)
*G01N 33/00* (2006.01)
*A61B 5/00* (2006.01)

(52) U.S. Cl. .......................................... 436/87; 436/86
(58) Field of Classification Search ................... 436/87, 436/86; 422/61, 50
See application file for complete search history.

(56) References Cited

U.S. PATENT DOCUMENTS

| 2003/0032200 A1 | 2/2003 | Herath et al. |
| 2005/0164238 A1 | 7/2005 | Valkirs et al. |
| 2005/0181451 A1 | 8/2005 | Bates |
| 2007/0003922 A1* | 1/2007 | Amaral et al. ................... 435/4 |
| 2007/0134814 A1 | 6/2007 | Kajander et al. |

FOREIGN PATENT DOCUMENTS

| WO | WO 01/63293 A2 | 8/2001 |
| WO | WO 2006/035237 A2 | 4/2006 |
| WO | WO 2006/085121 * | 8/2006 |
| WO | WO 2006/121952 A2 | 11/2006 |
| WO | WO 2006/125973 A2 | 11/2006 |

OTHER PUBLICATIONS

Finehout et al., Towards two-dimensional electrophoresis mapping of the cerebrospinal fluid proteome from a single individual, Electrophoresis, 2004, 25, 2564-2575.*
Schuchard et al., Specific Depletion of Twenty High Abundance Proteins from Human Plasma, NCI Proteomic Technologies, Reagents Resources Workshop, Dec. 12-13, 2005, pp. 1-2.*
Novikova et al., Identification of protein biomarkers for schizophrenia and bipolar disorder in the postmortem prefrontal cortex using SELDI-TOF-MS ProteinChip profiling combined with MALDI-TO-PSD-MS analysis, Neurobiology of Disease, 2006, 23, 6176.*
Barone et al., "Role of inflammation and cellular stress in brain injury and central nervous system diseases", Clinical Neuroscience Research, vol. 6, No. 5, Dec. 8, 2006, pp. 329-356.
Wong et al., "Acute phase proteins in male Chinese schizophrenic patients in Singapore", Schizophrenia Research, vol. 22, No. 2., 1996, pp. 165-171.
Sarafan, et al.,"The human inter-alpha-trypsin inhibitor genes respond differently to interleukin-6 in HepG2 cells", European Journal Biochem, Feb. 1995, vol. 227, No. 3, Abstract only, 1 pg.
Pineiro, et al., "ITIH4 (Inter-Alpha-Tryspin Inhibitor Heavy Chain 4) is a new acute-phase protein isolated from cattle during experimental infection", Infection and Immunity, Jul. 2004, vol. 72. No. 7, pp. 3777-3782.
International Search Report and Written Opinion mailed Nov. 18, 2008 in corresponding International application No. PCT/GB2008/000199.

* cited by examiner

*Primary Examiner* — Walter D Griffin
*Assistant Examiner* — Christine T Mui
(74) *Attorney, Agent, or Firm* — Gilberto M. Villacorta; Sunit Talapatra; Foley & Lardner LLP

(57) ABSTRACT

A method of diagnosing or monitoring a psychotic disorder, or predisposition thereto, comprises measuring, in a sample taken from a subject, the level of a biomarker selected from clusterin precursor, inter α-trypsin inhibitor, IgM, apolipoprotein A2 and α2 H5 glycoprotein.

6 Claims, No Drawings

METHODS AND BIOMARKERS FOR DIAGNOSING AND MONITORING PSYCHOTIC DISORDERS

CROSS-REFERENCE TO RELATED APPLICATIONS

This application is the U.S. National Phase of International Application PCT/GB2008/000199, filed Jan. 21, 2008, and published in English on Jul. 31, 2008, as WO 2008/090319; which claims benefit of the filing date of Great Britain Application No. 0701626.4, filed Jan. 22, 2007.

TECHNICAL FIELD

The present invention relates to methods of diagnosing or of monitoring psychotic disorders, in particular schizophrenic disorders (and bipolar disorders), e.g. using biomarkers. The invention also relates to use of biomarkers in clinical screening, assessment of prognosis, evaluation of therapy, drug screening and drug development. The biomarkers and methods in which they are employed can be used to assist diagnosis, and to assess onset and development of psychotic disorders.

BACKGROUND OF THE INVENTION

The identification of biomarkers for schizophrenic disorders permits integration of diagnostic procedures and therapeutic regimes. Currently, there are significant delays in determining effective treatment and it has not hitherto been possible to perform rapid assessment of drug response. Traditionally, many anti-schizophrenic therapies have required treatment trials lasting weeks to months for a given therapeutic approach.

WO2007/045865 (the content of which is incorporated by reference) describes psychosis and other disorders and the need for biomarkers. The biomarkers described there include ApoA1 (apolipoprotein) peptide.

Yang et al (2006), Anal. Chem. 78, 3571-6, discloses altered levels of proteins in the plasma of patients with schizophrenia. The results relate to markers of drug efficacy. There is apparently no difference between treated and non-treated patients. No quantitative results are given.

SUMMARY OF THE INVENTION

Based on an approach of the type described in WO2007/045865, ApoA1 has been confirmed as a biomarker, and others have been identified. According to one aspect of the invention, a method of diagnosing or monitoring a psychotic disorder, or predisposition thereto, comprises monitoring the level of one or more biomarkers present in a sample taken from a subject, the biomarkers including at least one defined in Tables 2 and 3, below.

Further aspects of the invention are defined in the claims, and/or are the same procedures/products as described for biomarkers in WO2007/045865. They include a method for monitoring efficacy of therapy for a schizophrenic disorder in a subject. Monitoring methods of the invention can be used to monitor onset, progression, stabilisation, amelioration and/or remission of a psychotic disorder.

Another aspect of the invention is a method of identifying a substance capable of stimulating, promoting or activating the generation of a peptide biomarker in a subject, comprising administering a test substance to a subject animal and detecting and/or quantifying levels of the peptide biomarker present in a test sample from the subject. Further aspects of the invention are the use of a substance or ligand according to the invention in the treatment of a schizophrenic disorder or predisposition thereto and as a medicament. The substance may be used according to the invention in the manufacture of a medicament for the treatment of a schizophrenic disorder or predisposition thereto.

DESCRIPTION OF THE INVENTION

In use of the invention, it will be appreciated that a single biomarker or more than one may be used, on one or more than one occasion, and with respect to one or more samples. For example, a combination of one or more biomarkers as shown in Table 2 and/or Table 3 may be used, as all or part of a "panel" of biomarkers. Reference may be made to protein biomarkers, and it will be appreciated that, according to circumstances, reference to such a protein includes fragments thereof.

In testing according to the invention, a changed or lower level of plasma protein biomarkers in a test biological sample relative to the level in a normal control is indicative of the presence of a psychotic disorder, in particular a schizophrenic disorder, bipolar disorder, or predisposition thereto. A decrease in the level of plasma protein in a biological sample, preferably in a sample of whole blood, plasma, or serum over time may be indicative of onset or progression, i.e. worsening of the disorder, whereas an increase in the level of plasma protein may indicate amelioration or remission of the disorder.

Methods of monitoring and of diagnosis according to the invention are useful to confirm the existence of a disorder, or predisposition thereto, to monitor development of the disorder by assessing onset and progression, or to assess amelioration or regression of the disorder. Methods of monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects), reducing "down-time" and relapse rates.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

Modulation of a peptide biomarker level is useful as an indicator of the state of the schizophrenic disorder or predisposition thereto. A decrease in the level of peptide biomarker over time is indicative of onset or progression, i.e. worsening of the disorder, whereas an increase in the level of peptide biomarker indicates amelioration or remission of the disorder.

Detection of a peptide biomarker of the invention can be used to screen subjects prior to their participation in clinical trials. The biomarker provides a means to indicate therapeutic response, failure to respond, unfavourable side-effect profile, degree of medication compliance and achievement of adequate serum drug levels. The biomarker may be used to provide warning of adverse drug response, a major problem encountered with all psychotropic medications. Biomarkers are useful in development of personalized brain therapies, as assessment of response can be used to fine-tune dosage, minimise the number of prescribed medications, reduce the delay in attaining effective therapy and avoid adverse drug reactions. Thus, by monitoring a biomarker of the invention, patient care can be tailored precisely to match the needs determined by the disorder and the pharmacogenomic profile of the patient; the biomarker can thus be used to titrate the optimal dose, predict a positive therapeutic response, and identify those patients at high risk of severe side effects.

Biomarker-based tests provide a first-line assessment of 'new' patients, and provide objective measures for accurate and rapid diagnosis, in a time frame and with precision, not achievable using the current subjective measures.

Furthermore, diagnostic biomarker tests are useful to identify family members or patients in the "prodromal phase", i.e. those at high risk of developing overt schizophrenia. This permits initiation of appropriate therapy, for example low dose antipsychotics, or preventive measures, e.g. managing risk factors such as stress, illicit drug use or viral infections. These approaches are recognised to improve outcome and may prevent overt onset of the disorder.

Biomarker monitoring methods, biosensors and kits are also vital as patient monitoring tools, to enable the physician to determine whether relapse is due to a genuine breakthrough or worsening of the disease, poor patient compliance or substance abuse. If pharmacological treatment is assessed to be inadequate, then therapy can be reinstated or increased. For genuine breakthrough disease, a change in therapy can be given if appropriate. As the biomarker is sensitive to the state of the disorder, it provides an indication of the impact of drug therapy or of substance abuse.

High-throughput screening technologies based on the biomarkers of the invention, uses and methods of the invention, e.g. configured in an array format, are suitable to monitor biomarkers for the identification of potentially useful therapeutic compounds, e.g. ligands such as natural compounds, synthetic chemical compounds (e.g. from combinatorial libraries), peptides, monoclonal or polyclonal antibodies or fragments thereof, capable of modulating the expression of the biomarkers.

The term "biomarker" means a distinctive biological or biologically derived indicator of a process, event or condition. Peptide biomarkers can be used in methods of diagnosis, e.g. clinical screening, and prognosis assessment; and in monitoring the results of therapy, for identifying patients most likely to respond to a particular therapeutic treatment, as well as in drug screening and development. Biomarkers and uses thereof are valuable for identification of new drug treatments and for discovery of new targets for drug treatment.

The term "drug-naïve patient" as used herein means an individual who has not been treated with any schizophrenia therapeutic substance. In a preferred embodiment, the invention relates to a method wherein the test sample is from a test subject wherein the test subject is a first onset drug-naïve individual, and the sample is taken prior to administration of any anti-schizophrenic therapy to the subject. The control sample is preferably a sample from a normal individual.

The term "diagnosis" as used herein encompasses identification, confirmation, and/or characterisation of a schizophrenic disorder or predisposition thereto. The term "predisposition" as used herein means that a subject does not currently present with the disorder, but is liable to be affected by the disorder in time. Methods of diagnosis according to the invention are useful to confirm the existence of a disorder, or predisposition thereto. Methods of diagnosis are also useful in methods for assessment of clinical screening, prognosis, choice of therapy, evaluation of therapeutic benefit, i.e. for drug screening and drug development.

The term "psychotic disorder" as used herein refers to a disorder in which psychosis is a recognised symptom, this includes neuropsychiatric (psychotic depression and other psychotic episodes) and neurodevelopmental disorders (especially Autistic spectrum disorders), neurodegenerative disorders, depression, mania, and in particular, schizophrenic disorders (paranoid, catatonic, disorganized, undifferentiated and residual schizophrenia) and bipolar disorders.

Biological samples that may be tested in a method of the invention include whole blood, blood serum or plasma, urine, saliva, cerebrospinal fluid (CSF) or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner.

A number of spectroscopic techniques can be used to generate spectra, according to the invention, including NMR spectroscopy and mass spectrometry. In preferred methods, spectral analysis is performed by NMR spectroscopy, preferably $^1$H NMR spectroscopy. One or more spectra may be generated; a suite of spectra may be measured, including one for small molecules and another for macromolecule profiles. The spectra obtained may be subjected to spectral editing techniques. One or two-dimensional NMR spectroscopy may be performed.

An advantage of using NMR spectroscopy to study complex biomixtures is that measurements can often be made with minimal sample preparation (usually with only the addition of 5-10% $D_2O$) and a detailed analytical profile of the whole biological sample can be obtained.

Sample volumes are small, typically 0.3 to 0.5 ml for standard probes, and as low as 3 µl for microprobes. Acquisition of simple NMR spectra is rapid and efficient using flow-injection technology. It is usually necessary to suppress the water NMR resonance.

High resolution NMR spectroscopy (in particular $^1$H NMR) is particularly appropriate. The main advantages of using $^1$H NMR spectroscopy are the speed of the method (with spectra being obtained in 5 to 10 minutes), the requirement for minimal sample preparation, and the fact that it provides a non-selective detector for all metabolites in the biofluid regardless of their structural type, provided only that they are present above the detection limit of the NMR experiment and that they contain non-exchangeable hydrogen atoms.

NMR studies of body fluids should ideally be performed at the highest magnetic field available to obtain maximal dispersion and sensitivity and most $^1$H NMR studies are performed at 400 MHz or greater, e.g. 600 MHz.

Usually, to assign $^1$H NMR spectra, comparison is made with control spectra of authentic materials and/or by standard addition of an authentic reference standard to the sample. The control spectra employed may be normal control spectra, generated by spectral analysis of a biological sample from a normal subject, and/or psychotic disorder control spectra, generated by spectral analysis of a biological sample from a subject with a psychotic disorder.

Additional confirmation of assignments is usually sought from the application of other NMR methods, including, for example, 2-dimensional (2D) NMR methods, particularly COSY (correlation spectroscopy), TOCSY (total correlation spectroscopy), inverse-detected heteronuclear correlation methods such as HMBC (heteronuclear multiple bond correlation), HSQC (heteronuclear single quantum coherence), and HMQC (heteronuclear multiple quantum coherence), 2D J-resolved (JRES) methods, spin-echo methods, relaxation editing, diffusion editing (e.g., both 1D NMR and 2D NMR such as diffusion-edited TOCSY), and multiple quantum filtering.

By comparison of spectra with normal and/or psychotic disorder control spectra, the test spectra can be classified as having a normal profile, a psychotic disorder profile, or a psychotic disorder predisposition profile.

Comparison of spectra may be performed on entire spectra or on selected regions of spectra. Comparison of spectra may involve an assessment of the variation in spectral regions responsible for deviation from the normal spectral profile and in particular, assessment of variation in one or more biomarkers within those regions.

A limiting factor in understanding the biochemical information from both 1D and 2D-NMR spectra of biofluids, such as plasma, is their complexity. The most efficient way to compare and investigate these complex multiparametric data is employ the 1D or 2D NMR metabonomic approach in combination with computer-based "pattern recognition" (PR) methods and expert systems.

Although the utility of the metabonomic approach is well established, its full potential has not yet been exploited. The metabolic variation is often subtle, and powerful analysis methods are required for detection of particular analytes, especially when the data (e.g., NMR spectra) are so complex.

Metabonomics methods (which employ multivariate statistical analysis and pattern recognition (PR) techniques, and optionally data filtering techniques) of analysing data (e.g. NMR spectra) from a test population yield accurate mathematical models which may subsequently be used to classify a test sample or subject, and/or in diagnosis.

Comparison of spectra may include one or more chemometric analyses of the spectra. The term "chemometrics" is applied to describe the use of pattern recognition (PR) methods and related multivariate statistical approaches to chemical numerical data. Comparison may therefore comprise one or more pattern recognition analysis methods, which can be performed by one or more supervised and/or unsupervised methods.

Pattern recognition (PR) methods can be used to reduce the complexity of data sets, to generate scientific hypotheses and to test hypotheses. In general, the use of pattern recognition algorithms allows the identification, and, with some methods, the interpretation of some non-random behaviour in a complex system which can be obscured by noise or random variations in the parameters defining the system. Also, the number of parameters used can be very large such that visualisation of the regularities or irregularities, which for the human brain is best in no more than three dimensions, can be difficult.

Usually the number of measured descriptors is much greater than three and so simple scatter plots cannot be used to visualise any similarity or disparity between samples. Pattern recognition methods have been used widely to characterise many different types of problem ranging for example over linguistics, fingerprinting, chemistry and psychology.

In the context of the methods described herein, pattern recognition is the use of multivariate statistics, both parametric and non-parametric, to analyse spectroscopic data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. The other approach is termed "supervised" whereby a training set of samples with known class or outcome is used to produce a mathematical model and this is then evaluated with independent validation data sets.

Unsupervised techniques are used to establish whether any intrinsic clustering exists within a data set and consist of methods that map samples, often by dimension reduction, according to their properties, without reference to any other independent knowledge, e.g. without prior knowledge of sample class. Examples of unsupervised methods include principal component analysis (PCA), non-linear mapping (NLM) and clustering methods such as hierarchical cluster analysis.

One of the most useful and easily applied unsupervised PR techniques is principal components analysis (PCA) (see, for example, Kowalski et al., 1986). Principal components (PCs) are new variables created from linear combinations of the starting variables with appropriate weighting coefficients. The properties of these PCs are such that: (i) each PC is orthogonal to (uncorrelated with) all other PCs, and (ii) the first PC contains the largest part of the variance of the data set (information content) with subsequent PCs containing correspondingly smaller amounts of variance.

PCA, a dimension reduction technique, takes m objects or samples, each described by values in K dimensions (descriptor vectors), and extracts a set of eigenvectors, which are linear combinations of the descriptor vectors. The eigenvectors and eigenvalues are obtained by diagonalisation of the covariance matrix of the data. The eigenvectors can be thought of as a new set of orthogonal plotting axes, called principal components (PCs). The extraction of the systematic variations in the data is accomplished by projection and modelling of variance and covariance structure of the data matrix. The primary axis is a single eigenvector describing the largest variation in the data, and is termed principal component one (PC1). Subsequent PCs, ranked by decreasing eigenvalue, describe successively less variability. The variation in the data that has not been described by the PCs is called residual variance and signifies how well the model fits the data. The projections of the descriptor vectors onto the PCs are defined as scores, which reveal the relationships between the samples or objects. In a graphical representation (a "scores plot" or eigenvector projection), objects or samples having similar descriptor vectors will group together in clusters. Another graphical representation is called a loadings plot, and this connects the PCs to the individual descriptor vectors, and displays both the importance of each descriptor vector to the interpretation of a PC and the relationship among descriptor vectors in that PC. In fact, a loading value is simply the cosine of the angle which the original descriptor vector makes with the PC.

Descriptor vectors which fall close to the origin in this plot carry little information in the PC, while descriptor vectors distant from the origin (high loading) are important for interpretation. Thus, a plot of the first two or three PC scores gives the "best" representation, in terms of information content, of the data set in two or three dimensions, respectively. A plot of the first two principal component scores, PC1 and PC2, provides the maximum information content of the data in two dimensions. Such PC maps can be used to visualise inherent clustering behaviour, for example, for drugs and toxins based on similarity of their metabonomic responses and hence mechanism of action. Of course, the clustering information may be in lower PCs and these can also be examined.

Hierarchical Cluster Analysis, another unsupervised pattern recognition method, permits the grouping of data points which are similar by virtue of being "near" to one another in some multidimensional space. Individual data points may be, for example, the signal intensities for particular assigned peaks in an NMR spectrum. A "similarity matrix" S, is constructed with element $ssij=1-rij/rijmax'$ where rij is the interpoint distance between points i and j (e.g., Euclidean interpoint distance), and rijmax is the largest interpoint distance for all points.

The most distant pair of points will have sij equal to 0, since rij then equals rijmaX. Conversely, the closest pair of points will have the largest sij, approaching 1. The similarity matrix is scanned for the closest pair of points. The pair of points is reported with their separation distance, and then the two points are deleted and replaced with a single combined point. The process is then repeated iteratively until only one point remains. A number of different methods may be used to determine how two clusters will be joined, including the nearest neighbour method (also known as the single link method), the furthest neighbour method, the centroid method (including centroid link, incremental link, median link, group average link, and flexible link variations).

The reported connectivities are then plotted as a dendrogram (a tree-like chart which allows visualisation of clustering), showing sample-sample connectivities versus increasing separation distance (or equivalently, versus decreasing similarity). In the dendrogram the branch lengths are proportional to the distances between the various clusters and hence the length of the branches linking one sample to the next is a measure of their similarity. In this way, similar data points may be identified algorithmically.

Supervised methods of analysis use the class information given for a training set of sample data to optimise the separation between two or more sample classes. These techniques include soft independent modelling of class analogy, partial least squares (PLS) methods, such as projection to latent discriminant analysis (PLS DA), k-nearest neighbour analysis and neural networks. Neural networks are a non-linear method of modelling data. A training set of data is used to develop algorithms that 'learn' the structure of the data and can cope with complex functions. Several types of neural network have been applied successfully to predicting toxicity or disease from spectral information.

Statistical techniques such as one-way analysis of variance (ANOVA) may also be employed to analyse data.

Methods of the invention involving spectral analysis may be performed to provide spectra from biological samples taken on two or more occasions from a test subject. Spectra from biological samples taken on two or more occasions from a test subject can be compared to identify differences between the spectra of samples taken on different occasions. Methods may include analysis of spectra from biological samples taken on two or more occasions from a test subject to quantify the level of one or more biomarkers present in the biological samples, and comparing the level of the one or more biomarkers present in biological samples taken on two or more occasions.

Diagnostic and monitoring methods of the invention are useful in methods of assessing prognosis of a psychotic disorder, in methods of monitoring efficacy of an administered therapeutic substance in a subject having, suspected of having, or of being predisposed to, a psychotic disorder and in methods of identifying an anti-psychotic or pro-psychotic substance. Such methods may comprise comparing the level of the one or more biomarkers in a test biological sample taken from a test subject with the level present in one or more samples taken from the test subject prior to administration of the substance, and/or one or more samples taken from the test subject at an earlier stage during treatment with the substance. Additionally, these methods may comprise detecting a change in the level of the one or more biomarkers in biological samples taken from a test subject on two or more occasions.

In methods of the invention, in particular those in which spectral analysis is employed, and in particular when the biological sample is blood or is derived from blood, e.g. plasma or serum, a suitable biomarker is as listed herein.

A method according to the invention may comprise comparing the level of one or more biomarkers in a biological sample taken from a test subject with the level present in one or more samples taken from the test subject prior to commencement of a therapy, and/or one or more samples taken from the test subject at an earlier stage of a therapy. Such methods may comprise detecting a change in the amount of the one or more biomarkers in samples taken on two or more occasions. Methods of the invention are particularly useful in assessment of anti-psychotic therapies.

A method of diagnosis of or monitoring according to the invention may comprise quantifying the one or more biomarkers in a test biological sample taken from a test subject and comparing the level of the one or more biomarkers present in said test sample with one or more controls. The control can be selected from a normal control and/or a psychotic disorder control. The control used in a method of the invention can be one or more controls selected from the group consisting of: the level of biomarker found in a normal control sample from a normal subject, a normal biomarker level; a normal biomarker range, the level in a sample from a subject with a schizophrenic disorder, bipolar disorder, related psychotic disorder, or a diagnosed predisposition thereto; a schizophrenic disorder marker level, a bipolar disorder marker level, a related psychotic disorder marker level, a schizophrenic disorder marker range, a bipolar disorder marker range and a related psychotic disorder marker range.

Biological samples can be taken at intervals over the remaining life, or a part thereof, of a subject. Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following an anti-psychotic therapy, such as an anti-schizophrenic or anti-bipolar disorder therapy.

Measurement of the level of a biomarker can be performed by any method suitable to identify the amount of the biomarker in a biological sample taken from a patient or a purification of or extract from the sample or a dilution thereof. Measuring the level of a biomarker present in a sample may include determining the concentration of the biomarker present in the sample. Such quantification may be performed directly on the sample, or indirectly on an extract therefrom, or on a dilution thereof. In methods of the invention, in addition to measuring the concentration of the biomarker in a biological sample, which is preferably whole blood, plasma or serum, the concentration of the biomarker may be tested in a different biological sample taken from the test subject, e.g. CSF, urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner.

Biomarker levels can be measured by one or more methods selected from the group consisting of: spectroscopy methods such as NMR (nuclear magnetic resonance), or mass spectroscopy (MS); SELDI (-TOF), MALDI (-TOF), a 1-D gel-based analysis, a 2-D gel-based analysis, liquid chromatography (e.g. high pressure liquid chromatography (HPLC) or low pressure liquid chromatography (LPLC)), thin-layer chromatography, and LC-MS-based techniques. Appropriate LC MS techniques include ICAT® (Applied Biosystems, CA, USA), or iTRAQ® (Applied Biosystems, CA, USA).

Measurement of a biomarker may be performed by a direct or indirect detection method. A biomarker may be detected directly, or indirectly, via interaction with a ligand or ligands, such as an enzyme, binding receptor or transporter protein, antibody, peptide, aptamer, or oligonucleotide, or any synthetic chemical receptor or compound capable of specifically binding the biomarker. The ligand may possess a detectable label, such as a luminescent, fluorescent or radioactive label and/or an affinity tag.

The term "antibody" as used herein includes, but is not limited to: polyclonal, monoclonal, bispecific, humanised or chimeric antibodies, single chain antibodies, Fab fragments and F (ab')$_2$ fragments, fragments produced by a Fab expression library, anti-idiotypic (anti-Id) antibodies, and epitopebinding fragments of any of the above. The term "antibody" as used herein also refers to immunoglobulin molecules and immunologically-active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

Metabolite biomarkers as described herein are suitably measured by conventional chemical or enzymatic methods (which may be direct or indirect and or may not be coupled), electrochemical, fluorimetric, luminometric, spectrophotometric, fluorimetric, luminometric, spectrometric, polarimetric, chromatographic (e.g. HPLC) or similar techniques.

For enzymatic methods, consumption of a substrate in the reaction, or generation of a product of the reaction, may be detected, directly or indirectly, as a means of measurement.

The biomarkers of the invention are preferably detected and measured using mass spectrometry-based techniques; chromatography-based techniques; enzymatic detection systems (by direct or indirect measurements); or using sensors, e.g. with sensor systems with amperometric, potentiometric, conductimetric, impedance, magnetic, optical, acoustic or thermal transducers.

A sensor may incorporate a physical, chemical or biological detection system. An example of a sensor is a biosensor, i.e. a sensor with a biological recognition system, e.g. based on a nucleic acid, such as an oligonucleotide probe or aptamer, or a protein such as an enzyme, binding protein, receptor protein, transporter protein or antibody.

The biosensor may incorporate an immunological method for detection of the biomarker, an electrical, thermal, magnetic, optical (e.g. hologram) or acoustic technologies. Using such biosensors, it is possible to detect the target biomarker at the anticipated concentrations found in biological samples.

Methods of the invention are suitable for clinical screening, assessment of prognosis, monitoring the results of therapy, identifying patients most likely to respond to a particular therapeutic treatment, for drug screening and development, and to assist in identification of new targets for drug treatment. The identification of key biomarkers specific to a disease is central to integration of diagnostic procedures and therapeutic regimes.

Methods of the invention may further comprise one or more assessments to diagnose and/or monitor a psychotic disorder in a subject. Assessment may be a clinical assessment, carried out by a clinician in accordance with accepted assessment protocols, e.g. global functioning score (GAF) or SCID, and/or may involve a self-assessment by the subject. Rating scales may be used to assist diagnosis and/or monitoring. GAF and SCID are assessed on the basis of a clinical interview. It is preferred that assessments, such as global functioning score, are made at (i.e. the same day as) or around (i.e. within a few days of) the time of collection of the test biological sample from the subject. This is particularly useful as a tool for diagnosing and monitoring female subjects, in which VLDL and LDL levels were found to have a very close inverse correlation with the clinical assessment as determined by global functioning score.

Using predictive biomarkers such as those described herein, appropriate diagnostic tools such as sensors and biosensors can be developed, accordingly, in methods and uses of the invention, detecting and quantifying one or more biomarkers can be performed using a sensor or biosensor.

The sensor or biosensor may incorporate detection methods and systems as described herein for detection of the biomarker. Sensors or biosensors may employ electrical (e.g. amperometric, potentiometric, conductimetric, or impedance detection systems), thermal (e.g. transducers), magnetic, optical (e.g. hologram) or acoustic technologies. In a sensor or biosensor according to the invention the level of one, two, or three biomarkers can be detected by one or more methods selected from: direct, indirect or coupled enzymatic, spectrophotometric, fluorimetric, luminometric, spectrometric, polarimetric and chromatographic techniques. Particularly preferred sensors or biosensors comprise one or more enzymes used directly or indirectly via a mediator, or using a binding, receptor or transporter protein, coupled to an electrical, optical, acoustic, magnetic or thermal transducer. Using such biosensors, it is possible to detect the level of target biomarkers at the anticipated concentrations found in biological samples.

A biomarker of the invention can be detected using a sensor or biosensor incorporating technologies based on "smart" holograms, or high frequency acoustic systems, such systems are particularly amenable to "bar code" or array configurations. In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of the biomarker of the invention are coupled, i.e. they combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect the biomarker of the invention include acoustic, plasmon resonance, holographic and microengineered sensors. Imprinted recognition elements, thin film transistor technology, magnetic acoustic resonator devices and other novel acousto-electrical systems may be employed in biosensors for detection of the biomarkers of the invention.

Methods involving detection and/or quantification of the biomarker of the invention can be performed using bench-top instruments, or can be incorporated onto disposable, diagnostic or monitoring platforms that can be used in a non-laboratory environment, e.g. in the physician's office or at the patient's bedside. Suitable sensors or biosensors for performing methods of the invention include "credit" cards with optical or acoustic readers. Sensors or biosensors can be configured to allow the data collected to be electronically transmitted to the physician for interpretation and thus can form the basis for e-neuromedicine.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

An increase in the level of the peptide biomarker in the test sample relative to the level in a previous test sample taken earlier from the same test subject is indicative of a beneficial effect, e.g. stabilisation or improvement, of said therapy on the disorder, suspected disorder or predisposition thereto.

Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following an anti-schizophrenic disorder therapy. Samples can be taken at intervals over the remaining life, or a part thereof, of a subject.

Quantifying the amount of the biomarker present in a sample may include determining the concentration of the peptide biomarker present in the sample. Detecting and/or quantifying may be performed directly on the sample, or indirectly on an extract therefrom, or on a dilution thereof.

Detecting and/or quantifying can be performed by any method suitable to identify the presence and/or amount of a specific protein in a biological sample from a patient or a purification of extract of a biological sample or a dilution thereof. In methods of the invention, quantifying may be performed by measuring the concentration of the peptide biomarker in the sample or samples. Biological samples that may be tested in a method of the invention include cerebrospinal fluid (CSF), whole blood, blood serum, urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. Preferably, the sample is CSF or blood serum. The samples can be prepared, for example where appropriate diluted or concentrated, and stored in the usual manner.

Detection and/or quantification of peptide biomarkers may be performed by detection of the peptide biomarker or of a fragment thereof, e.g. a fragment with C-terminal truncation, and/or with N-terminal truncation. Fragments are suitably greater than 4 amino acids in length. Preferably, fragments are in the range of from about 6 to about 50 amino acids in length.

The biomarker may be directly detected, e.g. by SELDI or MALDI-TOF. Alternatively, the biomarker may be detected, directly or indirectly, via interaction with a ligand or ligands such as an antibody or a biomarker-binding fragment thereof, or other peptide, or ligand, e.g. aptamer, or oligonucleotide, capable of specifically binding the biomarker. The ligand may possess a detectable label, such as a luminescent, fluorescent or radioactive label, and/or an affinity tag. Ligands include, for example:

(1) in vivo: T3, T4 (thyroid hormones), vitamin A (indirectly by interacting with serum retinol-binding protein), apolipoprotein A1 (ApoA1), noradrenaline oxidation products, and pterins.

(2) in vitro (most of them pharmacological agents): some non-steroidal anti-inflammatory drugs (NSAIDs), environmental pollutants, such as polyhalogenated biphenyls and thyromimetic compounds, xanthone derivatives as well as natural and synthetic flavonoids.

For example, methods relating to detecting, monitoring, diagnosing and/or quantifying can be performed by one or more methods selected from the group consisting of: SELDI(-TOF), MALDI (-TOF), a 1-D gel-based analysis, a 2-D gel-based analysis, Mass spec (MS), LC and LC-MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods for diagnosis or monitoring according to the invention may comprise analysing a biological sample, e.g. cerebrospinal fluid (CSF) or serum, by SELDI-TOF, MALDI-TOF and other methods using mass spectrometry to detect the presence or level of the peptide biomarker. Such techniques may be used for relative and absolute quantification and also to assess the ratio of the biomarker according to the invention with other biomarkers that may be present.

These methods are also suitable for clinical screening, prognosis, monitoring the results of therapy, identifying patients most likely to respond to a particular therapeutic treatment, for drug screening and development, and identification of new targets for drug treatment.

Surface-enhanced laser deionization ionization (SELDI) mass spectrometry is a powerful tool for identifying a characteristic "fingerprint" of proteins and peptides in body fluids and tissues for a given condition, e.g. drug treatments and diseases. This technology utilizes protein chips to capture proteins/peptides and a time-of-flight mass spectrometer (tof-MS) to quantitate and calculate the mass of compounds ranging from small molecules and peptides of less than 1,000 Da up to proteins of 500 kDa. Quantifiable differences in protein/peptide patterns can be statistically evaluated using automated computer programs which represent each protein/peptide measured in the biofluid spectrum as a coordinate in multi-dimensional space. This approach has been most successful in the field of clinical biomarker discovery as it can be used as a diagnostic tool without knowing the biomarkers' identity. The SELDI system also has a capability of running hundreds of samples in a single experiment. In addition, all the signals from SELDI mass spectrometry are derived from native proteins/peptides (unlike some other proteomics technologies which require protease digestion), thus directly reflecting the underlying physiology of a given condition.

Detecting and/or quantifying the peptide biomarker may be performed using any method based on immunological, peptide, aptamer or synthetic recognition. For example, the method may involve an antibody, or a fragment thereof capable of specific binding to the peptide biomarker.

Any suitable animal may be used as a subject. It may be a human or non-human animal, for example a non-human primate, horse, cow, pig, goat, zebrafish, sheep, dog, cat, fish, rodent, e.g. guinea pig, rat or mouse, an insect (e.g. *Drosophila*), amphibian (e.g. *Xenopus*) or *C. elegans*.

When used in a method of identification, the test substance can be a known chemical or pharmaceutical substance, such as, but not limited to, an anti-schizophrenic disorder therapeutic, or a synthetic or natural chemical entity, or a combination of two or more of the aforesaid substances.

Identifying a substance capable of stimulating, promoting or activating the generation of a peptide biomarker, in a subject, may comprise exposing a test cell to a test substance and monitoring levels of the peptide biomarker within said test cell, or secreted by said test cell. The test cell could be prokaryotic, however it is preferred that a eukaryotic cell be employed in cell-based testing methods. Suitably, the eukaryotic cell is a yeast cell, insect cell, *Drosophila* cell, amphibian cell (e.g. from *Xenopus*), *C. elegans* cell or is a cell of human, non-human primate, equine, bovine, porcine, caprine, ovine, canine, feline, piscine, rodent or murine origin. Non-human animals or cells can be used that are capable of expressing human polypeptides.

Screening methods also encompass a method of identifying a ligand capable of binding to a peptide biomarker according to the invention, comprising incubating a test substance in the presence of the peptide biomarker in conditions appropriate for binding, and detecting and/or quantifying binding of the peptide to said test substance.

High-throughput screening technologies based on the biomarkers, uses and methods of the invention, e.g. configured in an array, pattern or signature format, are suitable to monitor biomarker signatures for the identification of potentially useful therapeutic compounds, e.g. ligands such as natural compounds, synthetic chemical compounds (e.g. from combinatorial libraries), peptides, monoclonal or polyclonal antibodies or fragments thereof, capable of binding the biomarker.

Methods of the invention can be performed in array, pattern or signature format, e.g. on a chip, or as a multiwell array. As described above, other techniques, such as mass spectrometry can also be used. Methods can be adapted into platforms for single tests, or multiple identical or multiple non-identical tests, and can be performed in high throughput format. Methods of the invention may comprise performing one or more additional, different tests to confirm or exclude diagnosis, and/or to further characterise a condition.

The invention further provides a substance, e.g. a ligand, identified or identifiable by an identification or screening method or use of the invention. Such substances may be capable of stimulating, promoting or activating, directly or indirectly, the activity of a peptide biomarker, or of stimulating, promoting or activating generation of the peptide biomarker. The term substances includes substances that do not directly bind the peptide biomarker and directly induce expression of the peptide biomarker or promote or activate a function, but instead indirectly induce expression of the peptide biomarker or promote/activate a function of the peptide biomarker. Ligands are also included in the term substances; ligands of the invention (e.g. a natural or synthetic chemical compound, peptide, aptamer, oligonucleotide, antibody or antibody fragment) are capable of binding, preferably specific binding, to a peptide biomarker.

A kit for diagnosing or monitoring a schizophrenic disorder or predisposition thereto may contain one or more components selected from a ligand specific for a peptide biomarker, a peptide biomarker, controls, reagents, and consumables; optionally together with instructions for use of the kit.

The terms "treating" or "treatment" as used herein with reference to therapeutic uses of the biomarker of the invention describe the management or care of a patient for the purposes of combating disease, and include the administration of the active agents to asymptomatic individuals, for example to prevent the onset of the symptoms or complications (i.e. prophylaxis).

The term "therapeutic substance" as used herein defines a substance that has therapeutic, i.e. curative/beneficial properties and treats a schizophrenic disorder, alleviates the symptoms thereof or prevents the onset of a schizophrenic disorder. Thus, the substance is for use in the treatment of schizophrenia.

The following Examples include evidence on which the invention is based.

Example 1

This Example describes experimental records and protocol for discovery of protein biomarkers for schizophrenia in serum using label-free relative quantitation by LC-MS/MS 1. Clinical Samples Informed consent was given in writing by all participants and clinical investigations were conducted according to the principles expressed in the Declaration of Helsinki. Serum samples were collected from drug-naïve patients diagnosed with first episode paranoid schizophrenia or brief psychotic disorder due to duration of illness.

A total of 25 serum samples were analyzed: 13 first-onset drug-naïve schizophrenia patients and 12 healthy controls. The samples were stored at −80° C. and underwent a freeze-thaw cycle only once prior to preparation.

2. Sample Preparation

Serum samples were prepared blindly in random order using the following protocol:
  a) Each serum sample was depleted of the 20 most abundant proteins using the Sigma ProteoPrep20 immunoaffinity spin column kit.
    10 µl of serum was diluted with 90 µl of equilibrium buffer supplied with the kit.
    The diluted serum was filtered using a 0.22 µm filter at 4500 rpm for 1 minute.
    The filtered diluted serum was loaded onto the immunoaffinity column and incubated at room temperature for 15 minutes then centrifuged for 1 minute at 4500 rpm. 100 µl of equilibrium buffer was added to the column and spun at 4500 rpm for 1 minute. The last step repeated once more. A total of 300 µl flow through collected and stored at −80° C.
  b) Buffer exchange and sample concentration:
    a. Pre-rinsed a 5 k MWCO filter (Milipore) by freshly made 50 mM ammonium bicarbonate buffer (0.395 g in 100 mL, natural pH 7.8), centrifuged at 12,000 rpm for 5 minutes.
    b. Added the depleted serum sample onto the washed filter, 300 µL at a time, spun at 12,000 rpm for 15 minutes or until the volume was below 100 µL.
    c. After completing the concentration, topped up the filter to 0.5 mL using 50 mM ammonium bicarbonate buffer, pipetted the sample to prevent proteins from stacking onto the filter, spun at 12,000 rpm for 15 minutes. The washing procedure was repeated twice.
    d. The remaining volume was checked to make sure it was approx 100 µL. The sample was transferred to an eppendorf tube and stored at −80° C.
  c) Total protein concentration was measured using the Bio-Rad DC protein assay to each sample.
    a. Each sample was then digested using modified trypsin (Promega) in the following manner: Prepared 100 mM fresh DTT solution (15.4 mg in 1 mL water). Added 5 µL DTT solution to each sample. Vortexed to mix and incubated at 37° C. for 1 hour.
    b. Added trypsin solution (0.5 µg/µL) into each sample, based on the sample concentration measurement. The working ratio being trypsin:protein=1:25 (weight: weight).
    c. Vortexed to mix, incubated at 37° C. for 14 hours. Stored in −80° C.
  d) To stop the trypsin digestion, 10 µL of 1M Acetic acid was added to each digested sample (gives acid conc. ~100 mM). The final protein concentration was calculated based on the initial protein concentration. The samples were diluted with 99.9% $H_2O$+0.1% formic acid, so that 0.375 µg could be injected to LC-MS. 25 fmol/µl of yeast Enolase was spiked to each sample.

3. LC-MS/MS Analysis

The analysis was performed using Waters' Protein Expression System, which is comprised of a nano Ultra Performance Liquid Chromatography—the 10 kpsi nanoAcquity, coupled with a Quadrupole-Time-of-Flight Mass Spectrometer—the Qtof Premier.

Prior to analysis the system was tested for adequate sensitivity, resolution, retention time reproducibility and intensity reproducibility using digested Yeast Enolase (Waters). This was followed by analysis of two protein mixtures: one with unimolar concentrations and the other with regulated concentrations. The system identified the proteins to be regulated to within ±15%.

Samples were randomized in the freezer and 2-3 samples thawed a day. Each sample was injected 3 times with a blank injection and a standard injection in between, alternatively.
  a) Liquid Chromatography
  Mobile phase A: 99.9% $H_2O$+0.1% formic acid.
  Mobile phase A: 99.9% Acetonitrile+0.1% formic acid.
  Weak wash: 99.9% $H_2O$+0.1% formic acid.
  Strong wash: 99.9% Acetonitrile+0.1% formic acid.
  Autosampler temperature: 150° C.
  Column temperature: 400° C.

a. A total of 2 μl were injected on to the trapping column—180 μm×20 mm Symetry BEH nanoAcquity (Waters). Trapping was performed at 15 μl/min for 1 minute with 100% A.
b. The sample was then loaded onto the analytical column—nanoAcquity 75 μm×200 mm BEH 1.7 μm particles (Waters), using the gradient shown in Table 1.

TABLE 1

| Time (min) | Flow (ul/min) | % A | % B | Curve |
|---|---|---|---|---|
|  | 0.3 | 97 | 3 | 6 |
| 1 | 0.3 | 97 | 3 | 6 |
| 60 | 0.3 | 70 | 30 | 6 |
| 80 | 0.3 | 10 | 90 | 6 |
| 90 | 0.3 | 10 | 90 | 6 |
| 91 | 0.3 | 97 | 3 | 6 |
| 110 | 0.3 | 97 | 3 | 6 | b) Mass Spectrometry

Data was acquired in Expression (alternating collision energy without precursor ion isolation), positive V mode with the instrument tuned to 10000 FWHM resolution.
A reference scan was acquired every 30 scans.
Scan time: 0.6 sec; Mass range: 50 to 1990 m/z; low collision energy 4 ev, high collision energy 20-43 ev.

4. Data Processing

The following processing was performed on the raw data using Waters' ProteinLynx Global Server 2.2.5 (PLGS) software: smoothing, adaptive background subtraction, centering, deisotoping and mass correction.

The processed data was sent to a databank search using the human protein sequences from Swissprot databank version 50.8.

Relative quantitation and univariate analysis was performed in PLGS software.

Data was normalized using 7 peptides of the spiked Enolase.

The processed data was also exported to Simca P+ (Umetrics) for multivariate analysis (Partial Least Square-Discriminate Analysis).

The following results were obtained from analysis of 25 serum samples: 13 drug naïve schizophrenia patients and 12 healthy controls.

Most significant differentially expressed proteins:
Apo A IV (8 peptides):
  average 1.85 fold down-regulated.
Inter alpha trypsin inhibitor (5 peptides):
  average 1.49 fold down-regulated.
Serotransferrin precursor (3 peptides):
  average 1.78 fold down-regulated.
Clusterin precursor (2 peptides):
  average 1.58 fold down-regulated.

TABLE 2

| Description | Fold Change (Scz: Cont.) |
|---|---|
| P00751 Complement factor B precursor EC 3 4 21 47 C3 C5 convertase Properdin factor B Glyci | −1.92 |
| P02647 Apolipoprotein A I precursor Apo AI ApoA I Contains Apolipoprotein A I 1 242 | −1.35 |
| P02787 Serotransferrin precursor Transferrin Siderophilin Beta 1 metal binding globulin | −1.54 |
| P02787 Serotransferrin precursor Transferrin Siderophilin Beta 1 metal binding globulin | −1.35 |
| P02787 Serotransferrin precursor Transferrin Siderophilin Beta 1 metal binding globulin | −2.44 |
| P06727 Apolipoprotein A IV precursor Apo AIV ApoA IV | −1.64 |
| P06727 Apolipoprotein A IV precursor Apo AIV ApoA IV | −1.72 |
| P06727 Apolipoprotein A IV precursor Apo AIV ApoA IV | −1.89 |
| P06727 Apolipoprotein A IV precursor Apo AIV ApoA IV | −1.75 |
| P06727 Apolipoprotein A IV precursor Apo AIV ApoA IV | −2.17 |
| P06727 Apolipoprotein A IV precursor Apo AIV ApoA IV | −2.00 |
| P06727 Apolipoprotein A IV precursor Apo AIV ApoA IV | −1.59 |
| P06727 Apolipoprotein A IV precursor Apo AIV ApoA IV | −2.00 |
| P10909 Clusterin precursor Complement associated protein SP 40 40 Complement cytolysis inhibito | −1.64 |
| P10909 Clusterin precursor Complement associated protein SP 40 40 Complement cytolysis inhibito | −1.52 |
| P19823 Inter alpha trypsin inhibitor heavy chain H2 precursor ITI heavy chain H2 Inter alpha in | −1.37 |
| P19823 Inter alpha trypsin inhibitor heavy chain H2 precursor ITI heavy chain H2 Inter alpha in | −1.41 |
| P19823 Inter alpha trypsin inhibitor heavy chain H2 precursor ITI heavy chain H2 Inter alpha in | −1.37 |
| P19823 Inter alpha trypsin inhibitor heavy chain H2 precursor ITI heavy chain H2 Inter alpha in | −1.47 |
| P19823 Inter alpha trypsin inhibitor heavy chain H2 precursor ITI heavy chain H2 Inter alpha in | −1.82 |

Example 2

Using a procedure similar to Example 1, 55 samples (22 schizophrenia patients, 33 controls), the putative peptide biomarkers given in Table 3 were found (* indicates depleted by antibodies).

TABLE 3

| Ig Mu* | p value 0.0011 |
|---|---|
| Apolipoprotein A1* | p value 0.0175 |
| Apolipoprotein A2* | p value 0.0253 |
| Serotransferrin* | p value 0.0320 |
| Alpha-2-H5-glyconprotein precursor | p value 0.0323 |

The invention claimed is:

1. A method of diagnosing or monitoring in a subject a psychotic disorder, a predisposition thereto, or monitoring efficacy of therapy thereof, comprising measuring, in a sample taken from the subject, the level of at least one first biomarker selected from (a) serotransferrin or a precursor thereof and (b) inter α-trypsin inhibitor, wherein the level of the biomarker is indicative of a psychotic disorder, a predisposition thereto, or the efficacy of therapy thereof, and wherein the indication of the psychotic disorder, or a predisposition thereto in the subject comprises a down-regulation of the level of serotransferrin or a precursor thereof, or inter α-trypsin inhibitor, or both, in the subject relative to a normal control.

2. The method of claim 1, wherein the indication of the psychotic disorder, or a predisposition thereto, in the subject further comprises down-regulation of the level of ApoA IV, clusterin precursor, or both, in the subject relative to a normal control.

3. The method of claim 1, wherein the down-regulation of the level of serotransferrin, or a precursor thereof, is an average of 1.78 fold.

4. The method of claim 1, wherein the down-regulation of the level of inter α-trypsin inhibitor is an average of 1.49 fold.

5. The method of claim 2, wherein the down-regulation of the level of ApoA IV is an average of 1.85 fold.

6. The method of claim 2, wherein the down-regulation of the level of clusterin precursor is an average of 1.58 fold.

* * * * *

UNITED STATES PATENT AND TRADEMARK OFFICE
CERTIFICATE OF CORRECTION

| | |
|---|---|
| PATENT NO. | : 7,981,684 B2 |
| APPLICATION NO. | : 12/523842 |
| DATED | : July 19, 2011 |
| INVENTOR(S) | : Yishai Levin et al. |

It is certified that error appears in the above-identified patent and that said Letters Patent is hereby corrected as shown below:

Column 16, line 65 (last row of Table 3), "H5" should read --HS--.

Signed and Sealed this
Thirteenth Day of March, 2012

David J. Kappos
*Director of the United States Patent and Trademark Office*